United States Patent [19]

Lynn

[11] Patent Number: 5,390,553
[45] Date of Patent: Feb. 21, 1995

[54] LIQUID SAMPLING APPARATUS AND METHOD

[76] Inventor: Lewis G. Lynn, 65 Hillhurst La., Rochester, N.Y. 14617

[21] Appl. No.: 995,572

[22] Filed: Dec. 22, 1992

[51] Int. Cl.⁶ ............................................. G01N 1/10
[52] U.S. Cl. .................. 73/864.91; 73/863.11; 141/316
[58] Field of Search ......... 73/864.51, 864.91, 863.52, 73/864.62, 864.63, 863.11; 141/316

[56] References Cited

U.S. PATENT DOCUMENTS

| | | | |
|---|---|---|---|
| 2,475,857 | 7/1949 | Reinert | 73/864.91 X |
| 3,635,091 | 1/1972 | Linzer et al. | 604/409 X |
| 3,762,542 | 10/1973 | Grimes | 206/525 |
| 3,819,107 | 6/1974 | Ryder, Jr. | 206/219 |
| 3,961,529 | 6/1976 | Henifl | 73/219 X |
| 4,009,617 | 3/1977 | Johnson | 73/863.84 |
| 4,151,929 | 5/1979 | Sapien | 220/404 |
| 4,252,256 | 2/1981 | Walsh | 383/121.1 X |
| 4,485,855 | 12/1984 | Dillingham | 141/316 |
| 4,548,087 | 10/1985 | Huck | 73/863.57 |
| 5,210,994 | 5/1993 | Lynn | 144/313 X |

*Primary Examiner*—Tom Noland
*Attorney, Agent, or Firm*—Shlesinger, Fitzsimmons & Shlesinger

[57] ABSTRACT

A liquid sampler bottle is provided with a removable, disposable, plastic bag liner which is sealed closed, when manufactured, and which, when placed in use, has a narrow neck section a portion of which is removed to open the plastic bag, after which the neck section is folded down around the neck of the bottle and held releasably in place while being filled with liquid. After the bag is filled it is sealed closed, and the bottle, which is made from at least two different sections which are releasably connected to each other, is dismantled by removing one section from the other in order to permit the sealed bag containing the sample to be removed from the bottle and transported to a laboratory or the like. The bottle can then be reassembled and utilized with a different bag without requiring any washing of the bottle.

8 Claims, 4 Drawing Sheets

LIQUID SAMPLING APPARATUS AND METHOD

BACKGROUND OF THE INVENTION

This invention relates to liquid sampling apparatus, and more particularly to improved means for collecting liquid samples. Even more particularly, this invention relates to a novel liquid sample container and disposable liner therefor.

Fluid sampling devices, and more particularly liquid sampling devices, generally utilize sample storage bottles for storing and transporting fluid samples, such as for example wastewater, water from a stream or river, or liquid effluent from a commercial or manufacturing enterprise. The sample storage bottles, usually are made from glass or plastic and come in a variety of shapes; but regardless of their particular configuration they share the same major problem—i.e., each container must be carefully cleaned after a sample is discharged therefrom so that the container will not contaminate any future samples stored therein.

The very need for having to clean the sample containers after each use contributes significantly to the overall cost of conventional sampling apparatus. Moreover, in those cases where even the slightest contamination must be avoided, it often is necessary to use more expensive glass containers, rather than plastic sample containers, because as a general rule the glass containers are easier to clean than plastic containers, and are not likely to exhibit any surface adsorption which might otherwise occur in less expensive, plastic containers.

It is an object of this invention, therefore, to provide an improved fluid or liquid sample container which will obviate the need for washing the container after each use thereof.

Still another object of this invention is to provide improved liquid sample containers of the type described which are particularly adapted for use with existing fluid sampling apparatus, and do not require cleaning after use.

A more specific object of this invention is to provide an improved liquid sample container which includes a generally rigid, bottle member, and a disposable, plastic liner removably inserted into the rigid container to receive and store a liquid sample therein.

Other objects of the invention will be apparent hereinafter from the specification and from the recital of the appended claims, particularly when read in conjunction with accompanying drawings.

SUMMARY OF THE INVENTION

In one embodiment a liquid sample bottle is made in two separate parts, upper and lower, which are releasably connected to each other. In use a sealed, flexible, plastic bag which is similar in configuration to the bottle is inserted into the bottle through the mouth thereof. The neck of the bag is then cut open and folded over the neck of the bottle where it is held by an annular collar that is press fit over the neck of the bottle. After the bag has been filled with a sample liquid the collar is removed, the neck of the bag is sealed closed, and the two sections of the bottle are separated to allow removal of the sealed bag which can then be delivered to a laboratory or the like to permit analysis of its liquid contents.

In a second embodiment the bottle is made in one piece and is cylindrical in configuration and has a mouth large enough to permit the bag with a liquid sample therein to be removed without dismantling the bottle.

DETAILED DESCRIPTION OF THE PREFERRED EMBODIMENTS

Figure 1:
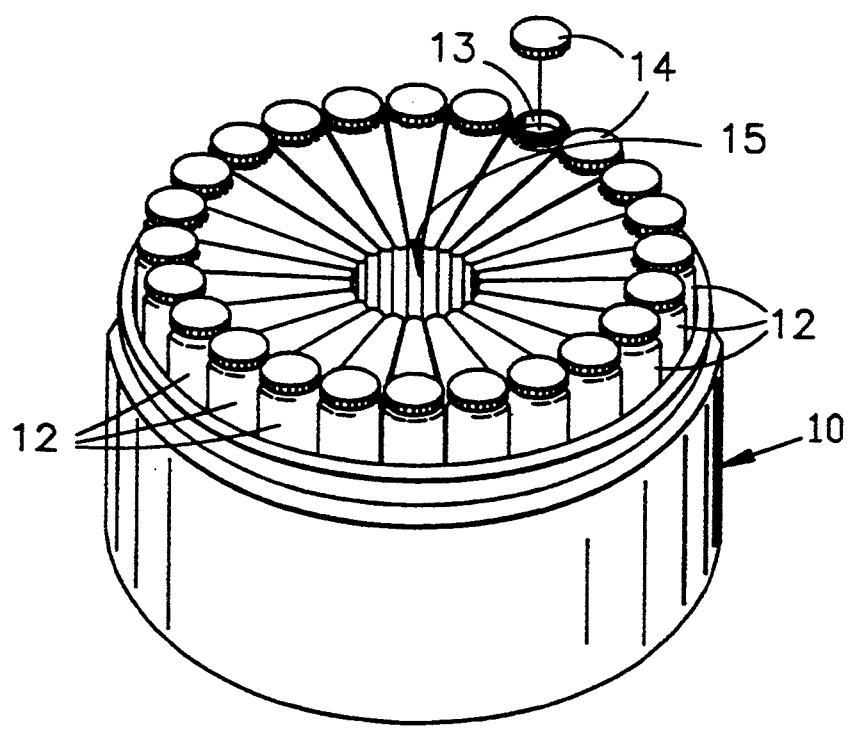
FIG. 1 is a perspective view of the base of a conventional sampler apparatus containing a plurality of sampler bottles or containers of conventional design.
Figure 2:
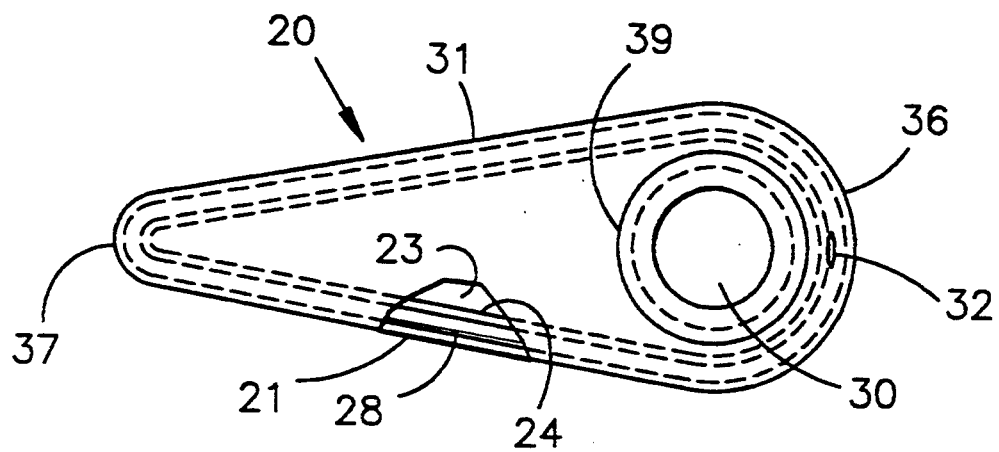
FIG. 2 is a plan view of an improved such sampler bottle made according to one embodiment of this invention.

Referring now to the drawings by numerals of reference, and first to FIG. 1, 10 denotes a bottle holding base which forms part of a conventional waste water sampler for which this invention is particularly suited. As illustrated in FIG. 1, base 10 contains a plurality of like containers or bottles 12, which are designed to contain wastewater samples or the like. Each container has in its upper end, and adjacent the outer edge thereof as shown in FIG. 1, an opening 13 which is adapted to be covered by a cap 14 that is releasably fastened over the associated opening 13. Bottles 12 are generally wedge-shape in cross section, and have curved, narrow inner edges positioned to form in the center of base 10 a cylindrical well which is denoted generally by the numeral 15. Well 15 is disposed to have stored therein a quantity of ice for chilling the contents of the bottles 12. For this reason also the base 10 is watertight, even when assembled, so that cold ice water which accumumlates in the base remains in contact with the bottles 12 and will not leak out of the base.

Referring now to FIGS. 2, 3 and 6, 20 denotes generally an improved liquid sampler bottle or container which is generally similar in overall configuration to the wedge-shaped bottles 12 as shown in FIG. 1, and which is designed to be used in place of such bottles. More specifically, bottle 20 comprises two separable bottle sections 21 and 31, each of which may be made from a plastic material such as polypropylene. The lower section 21 has a flat, generally wedge-shaped bottom wall section 23, which is integral with the lower ends of a pair of upstanding, spaced side wall sections 24 and 25, and upstanding, curved end wall sections 26 and 27. End wall 26 lies in an arcuate plane having a radius which is slightly larger than the radius of the end wall 27, so that the side walls 24 and 25 are inclined slightly toward each other as they extend from wall 26 to wall 27, thus giving the lower section 21 of the bottle the generally wedge-shaped configuration referred to above. The wedge-shaped section 21 is open at its upper end and has projecting centrally from the upper edge thereof an integral rib or boss 28, which extends completely around the upper end of section 21. As shown more clearly in FIG. 3, the boss 28 is nearly keyhole shaped in cross section for a purpose noted hereinafter.

The upper bottle section. 31 is also generally wedge-shaped in configuration and has a pair of spaced side walls 34 and 35 which register vertically with the side walls 24 and 25, respectively of section 21, and a pair of curved end walls 36 and 37 at least the lower end portions of which register vertically with the end walls 26 and 27, respectively, of section 21. The lower end of the bottle section 31 is open, and has formed in its lower edge centrally thereof a generally keyhole-shaped recess 38, which extends completely around the lower end of section 31. As shown more clearly in FIGS. 3 and 6, the boss 28 is removably and snugly seated within the correspondingly shaped recess 38, so that the confronting ends of sections 21 and 31 (i.e., the upper end of section 21 and the lower end of section 31) are sealingly and releasbly secured against each other along a seam S. Adjacent its upper end the upper bottle section 31 has formed thereon by a merger of its walls 34–37 an integral, cylindrical neck 39 having therethrough a central bore which forms an opening 30 (FIG. 2) in the upper end of the bottle 20. Just below its neck 39 the upper bottle section 31 has a small vent opening 32 formed through its end wall 36 for a purpose noted hereinafter.

Figures 3, 4:
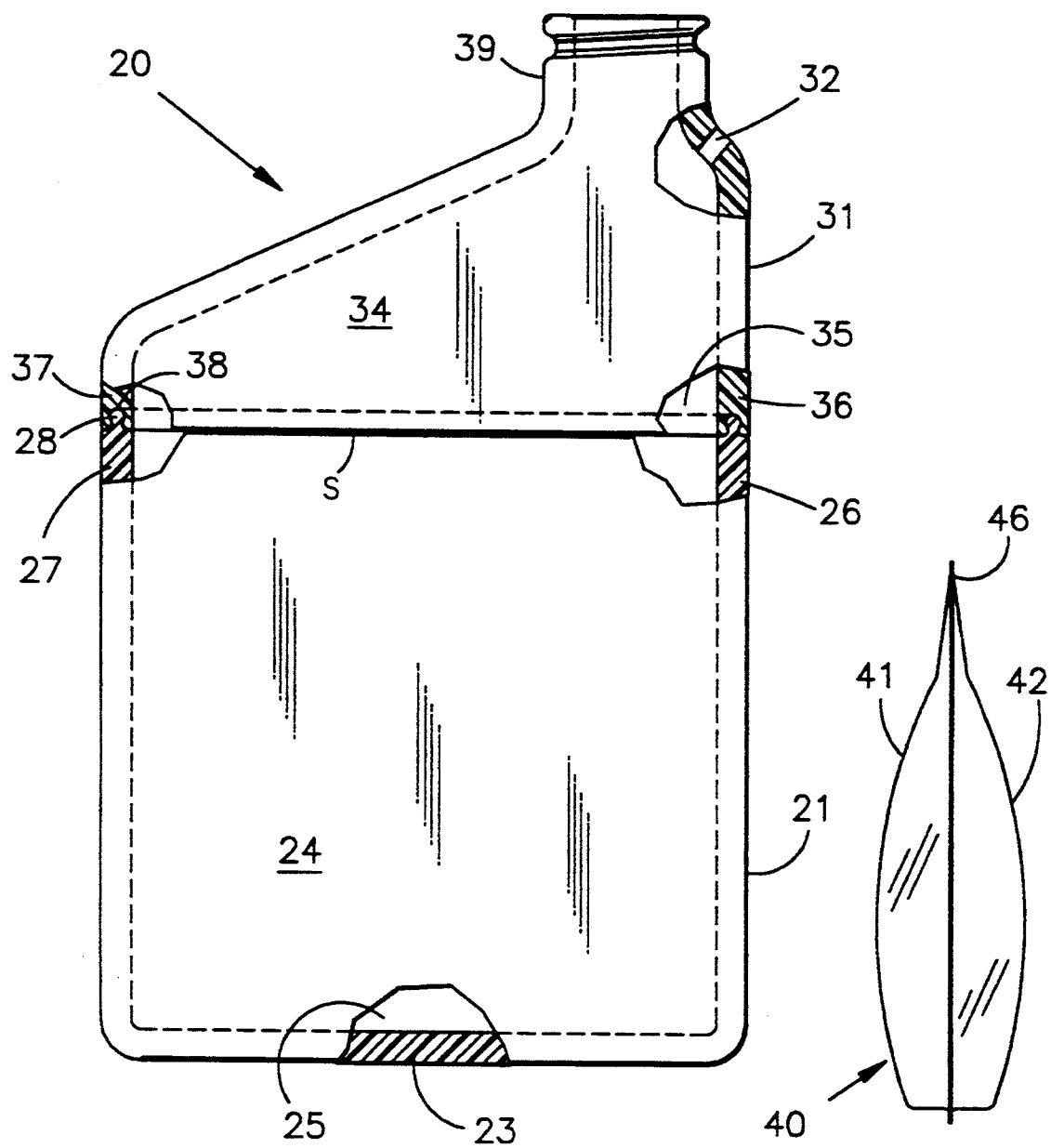
FIG. 3 is a front elevational view of this bottle on a slightly smaller scale, and with portions thereof cut away and shown in section.
FIG. 4 is a side elevational view of a disposable plastic bag of the type which is adapted to be employed in combination with this bottle.
Figure 5:
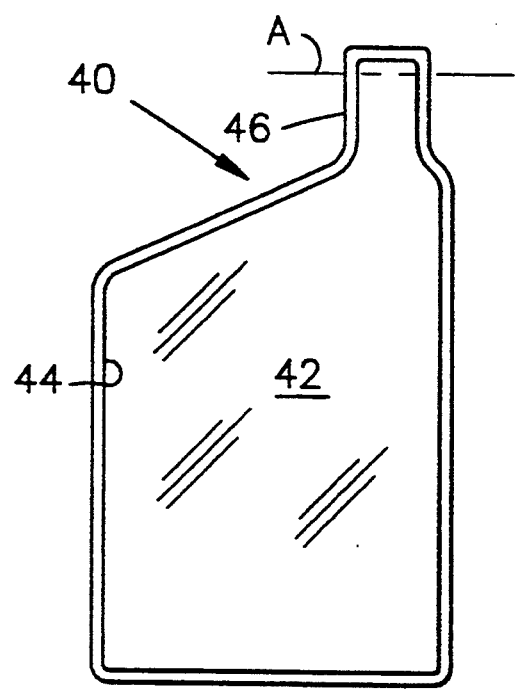
FIG. 5 is a side elevational view of this plastic bag.

Each bottle 20 is adapted to be employed with a disposable, flexible, plastic bag of the type illustrated, by way of example, in FIGS. 4 and 5, and denoted generally by the numeral 40. Bag 40 may be made from, for example, two like sheets 41 and 42 of flexible, theremoplastic material which in profile are similar in configuration to the profile of the bottle 20. The two sheets 41 can be sealed together along a seam 44 which extends around their marginal edges and which, until used, completely seals the bag 40 closed, including its reduced-diameter neck section 46. When the bag 40 is expanded or opened, as noted hereinafter, its neck section 46 will have an outside diameter approximately equal to the inside diameter of the neck 39 of bottle 20.

Figure 6:
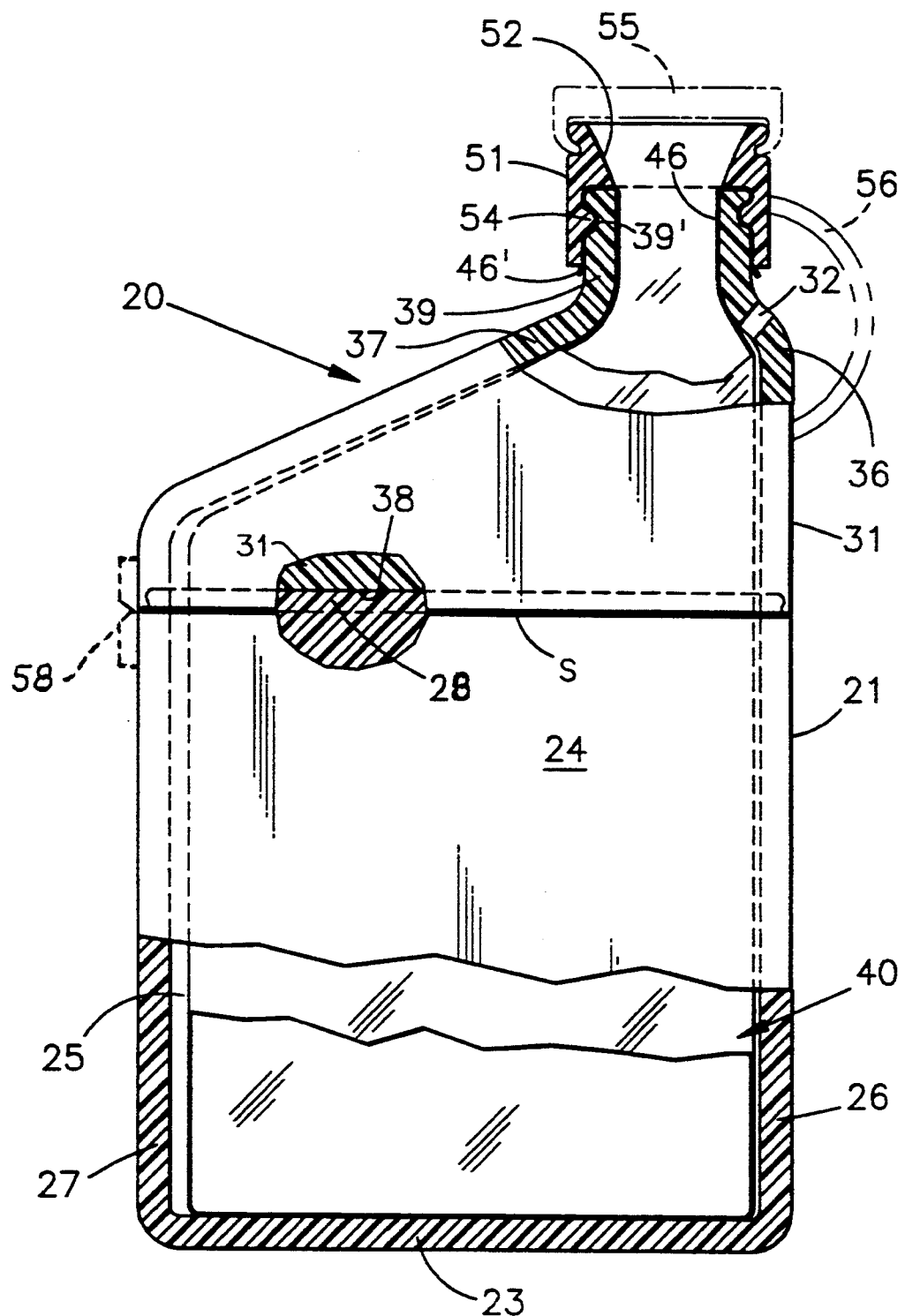
FIG. 6 is a fragmentary side elevational view of a bottle of the type shown in FIG. 3 after a bag of the type shown in FIGS. 4 and 5 has been releasably secured in the bottle for receiving a liquid sample or the like, portions of the bag and bottle being broken away and shown in section.

Each bag 40 is designed to be inserted into a bottle 20 to line the interior thereof, and to contain all of the sample fluid or liquid which otherwise normally would fill and contact the inner peripheral surface of the bottle 20 itself. Therefore, before being used, the upper end of each bag 20 is severed approximately along the line denoted at A in FIG. 5, thereby opening the neck portion 46 of the bag. The bag is then inserted into a bottle 20, as shown for example in FIG. 6, to line the interior of the bottle, and also to have the upper end of its neck portion 46 folded downwardly and over the outside of the bottle neck 39 as at 46' (FIG. 6). To secure the neck portion 46 removably around the bottle neck 39, an annular, plastic retaining collar 51, which has therethrough an axial bore 52 that registers with the bore in the bottle neck 39, is press fit snugly over the downwardly folded portion 46' of the bag. This connection is enhanced by a circumferential, annular bead 54, which is formed on the inner periphery of the collar 51 to urge a registering portion of the bag section 46' into an annular groove 39', which is formed in the outer periphery of the bottle neck 39.

When a bag 40 has been thus assembled into the bottle 20, it can be filled with a predetermined quantity of wastewater or the like. Thereafter the collar 51 is removed and, if desired, the neck portion 46' of the bag 40 is folded upwardly from around the outside of the bottle neck 39, and is sealed at its upper end, for example by heat sealing, thereby to seal the liquid sample entirely within the bag. Then, if it is desired to transport the sample in the bag to another locale, the top section 31 of the bottle 20 can be removed manually from the lower section 21 by applying sufficient pressure to the top section 31 to cause the bead 28 to become dislodged or released from the recess 38, after which the upper section 31 can be removed from the bag 20 by lifting section 31 upwardly to expose substantially the upper half of the now-filled bag 40. The bag 40 can then be removed from the lower section 21 of the bottle 20, after which the upper section 31 can be releasably snapped back into sealing engagement with the lower section 21. The reassembled bottle 20 can then be used once again, as noted above, for receiving another bag 40, which subsequently can be filled, sealed and removed again from the bottle 20 as noted above.

Rather then removing the filled bag 40 immediately from a bottle 20, the collar 51 can, if desired, be covered by a plastic cap 55, or the like, which is shown in phantom by broken lines in FIG. 6. The entire bottle 20 with the filled bag therein can then be removed from the base 10 of the sampling apparatus for transport to another location where the cap 55 can be removed and the sample in the bag 40 can be dumped or otherwise disposed of, after which the once-used bag 40 can be removed from the bottle 20 and discarded.

It is to be noted that during the filling of a bag 40 in a bottle 20, any air which may be interposed between the bag and the inner wall of the bottle will be exhausted out of the vent 32, so that no air will be trapped within the bottle to prevent expansion of the bag 40 as it is filled with a liquid sample. In addition, if desired, the collar 51 may be permanently attached to the upper section 31 of the bottle 20 by a strap 56, or the like, which is shown in phantom by broken lines in FIG. 6; and the two bottle sections 21 and 31 may be hinged together along one edge thereof, as shown for example by the hinge 58, which is shown in phantom by the broken lines in FIG. 6.

Figure 7:
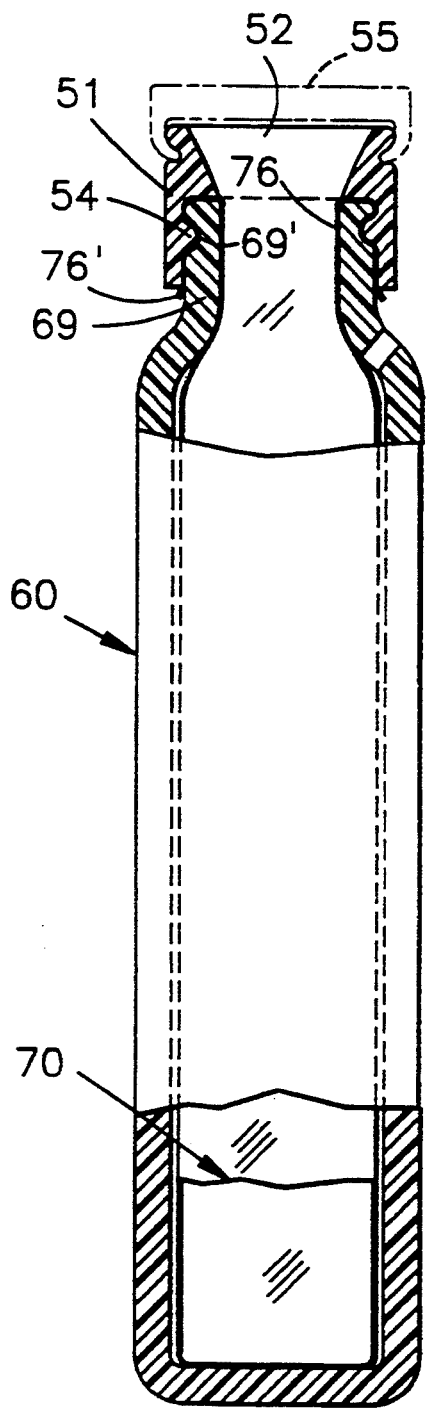
FIG. 7 is a view generally similar to FIG. 6 but showing a bottle and bag liner therefor made according to a second embodiment of this invention.

In the above-described embodiment the liquid-containing section of a bag 40 is substantially larger than its neck section 46 and the bottle neck 39. Consequently, when the bag has been filled with a liquid sample, and has therefore expanded into contact with a substantial portion of the inner surface of the bottle, it obviously is necessary in some way to dismantle the bottle if the filled bag is to be removed therefrom. However, when a cylindrical sampler bottle 60 is employed as shown in FIG. 7, it is possible to use a generally cylindrically shaped bag 70 for holding a sample.

In use, the neck section 76 of the bag 70 is adapted to be folded downwardly over the outside of the neck 69 of the bottle 60, and is releasably secured in this open position by a collar 51 which, as in the first embodiment, has an annular boss 54 which urges a registering portion of bag 70 into an annular recess 69' in the bottle neck 69. When bag 70 has been filled it may be closed by a cap 55 (broken lines in FIG. 7), or the collar 51 may be removed and the neck section 76 may be sealed closed as in the first embodiment. However, with this second embodiment, since the diameter of the filled, now-sealed bag 70 is approximately equal to the inside diameter of the bottle neck 69, it is possible to pull the filled bag out of bottle 60 through its open, upper end without dismantling the bottle.

From the foregoing it will be apparent that the present invention provides a relatively simple and inexpensive method and means for collecting liquid wastewater samples and the like. While utilzing the novel collector bottles and liners therefor as disclosed herein, it is possible to eliminate the need for thoroughly cleaning sampler bottles after each collection of a sample. The reason, of course, is that the sample liquid never touches the inside surface of the sampler bottle but instead is enclosed completely within a disposable bag. The bag has configuration which conforms, in essence, to the inner surface of the bottle when the bag is substantially filled with a liquid sample. Moreover, as noted above, in those instances where it is desirable to be able to remove a filled plastic bag from an associated sampler bottle, it is necessary in certain cases to manufacture the bottle in at least two separate sections, so that the bottle can be dismantled after the plastic bag therein has been filled with a liquid sample. Once dismantled, the filled and sealed plastic bag can then be removed from the bottle and transported to a laboratory, or the like, and without having thus to transport both the bottle and the filled bag to the laboratory. This not only reduces the cost of transportation and handling, but, in addition, eliminates the need also for having to wash the sampler bottle after each use.

When the sampler bottles are employed with sampler apparatus of the type disclosed in FIG. 1, the ice which is stored in the well 15 tends to melt and fill the base 12 with cold water. This water in turn exerts pressure against the external surfaces of the bottles 12, so that it is therefore important to manufacture the multi-section bottles 20 in such manner that the cold water in the base 10 will not leak into a bottle and possibly prevent the bag 40 therein from being completely filled with the sample.

Still another advantage of the invention is that it is a relatively simple matter to mass produce bags of the type denoted at 40 or 70 in the drawings, and in such manner that the bags will be completely sealed up until the time they are placed in use. At such time, of course, a portion of the neck section of the bottle is removed, such as for example by cutting the neck section 46 along the line A in FIG. 5 in order to open the bag. Since the bags are sealed closed until used, it is not necessary to clean the inside of the bag prior to its use.

While this invention has been illustrated and described in connection with only certain bottle shapes and bag shapes, it will be apparent to one skilled in the art that the exact shapes of the bottles and the associated bags can be changed without departing from this invention. Moreover, while the base 10 of FIG. 1 has been shown to contain twenty-four bottles, it will be understood that this number may change depending on the size and shapes of the bottles. In practice samplers also have been designed to hold 1, 2, 4, 6, 8 or 12 bottles, respectively, depending upon bottle configuration. Also, while base 10 has been shown to be of the type which employs ice for chilling, it is to be understood that the invention will apply equally as well to sample bottles which are held by racks in samplers of the type which utilize electrical refrigeration, rather than ice, for chilling samples.

In addition, it will be apparent that the exact manner in which the bags 40 and 70 are manufacutured, and the material from which they are made, can be altered without departing from this invention. For example, the bag material will be selected in accordance with the material best compatible for sample liquids suspected of having certain pollutants. This permits the invention to be used with Priority Samples (samples with low centrations of pollutants) where the container must not react with the sample and thus change its characteristics. By using the proper material for the bags, it will be possible to meet these more strigent sampling needs, and will reduce the need for using glass containers, which are currently employed for certain sampling procedures because glass exhibits substantially no surface adsorption, and has less tendency, as compared to some plastics, to react with sample pollutants. Glass containers, however, have the disadvantage of being fragile, rather heavy, and difficult to clean.

While this invention has been illustrated and described in detail in connection with only certain embodiments thereof, it will be apparent that it is capable of further modification, and that this application is intended to cover any such modifications as may fall within the scope of one skilled in the art or the appended claims.

The claims:

1. In a wastewater sampler including a housing and a plurality of similarly shaped liquid sample collectors arranged removably in said housing to form therein a space for accommodating in said housing a supply of ice for cooling the contents of said collectors, the improvement wherein each of said collectors comprises
   a generally rigid, hollow container having a closed lower end seated in said housing, and having at its upper end a cylindrically shaped neck section projecting upwardly in said housing and forming an opening in the upper end of said container,
   a flexible, plastic bag removably mounted in said container and having an inlet/outlet opening in an upper end thereof for admitting a liquid sample selectively into and out of said bag,
   bag supporting means releasably engaging and securing marginal portions of said bag around said inlet/outlet opening thereof to marginal portions of said neck section of said container around said opening in said upper end, thereby to support said bag upright in said container and with the inlet/outlet opening in said bag held open to permit the insertion of a liquid sample into said bag substantially to fill the latter,
   said bag supporting means being removable from engagement with said marginal portions of said neck section of said bag after said bag has been filled with liquid sample, thereby to permit the filled bag to be removed from said container, and
   said container having therein adjacent said neck section thereof a small vent hole communicating at one end with a space between said container and said bag at its opposite end with the exterior of said container.

2. A liquid sample collector as defined in claim 1, wherein
   said bag has a relatively narrow neck section containing said inlet/outlet opening, and a larger body section communicating with said neck section of said bag and disposed substantially to fill the interior of said container when filled with a liquid sample, and
   a first portion of said container is movable relative to a second portion thereof between a closed position in which said first and second portions engage and support said bag, when said bag is filled with a liquid sample, and an open position in which said first portion of said container is spaced from said second portion thereby to create in said container a second opening larger than said opening in the upper end of said container, and through which a filled bag may be withdrawn from said container upon release of said bag supporting means.

3. A liquid sample collector as defined in claim 2, wherein said first portion of said container is hingedly connected adjacent one edge thereof to an adjacent edge of said second portion, thereby to permit said first portion to be swung between its open and closed positions relative to said second portion of said container.

4. A method of collecting liquid samples, comprising
providing a plurality of rigid, hollow containers each having an opening in one end thereof surrounded by an annular neck portion of the container,
inserting in each of said containers an empty, flexible, plastic bag having in one end thereof an opening surrounded by an annular neck portion of the bag,
releasably securing the annular neck portion of each of said bags against said neck portion of its associated container so that the neck portion of said container supports said bag upright in said container with the neck portion of said bag held open,
filling said bags through the open neck portions thereof with liquid samples, whereby said bags prevent the sample liquids therein from contacting said containers,
sealing the neck portions of said bags closed to seal the sample liquids therein,
removably storing said containers and their sealed bags in a housing containing a coolant for cooling the samples in said bags, and
thereafter removing the sealed bags from said containers without destroying the containers, whereby the above-noted steps may be repeated using the same containers.

5. The method as defined in claim 4 wherein
each of said containers has therein a second, normally closed opening larger than the first-named opening therein, and
momentarily opening said second openings in said containers and withdrawing the filled sample bags through said second openings.

6. The method as defined in claim 4, wherein each of said containers comprises two sections, one of which sections contains said neck portion of the container, and the other of which sections is removably connected to said one section during the filling of the associated bag with said liquid sample, and the step of removing said bags from said containers, includes,
disconnecting said other section of a container from said one section thereof after the associated bag has been filled with a liquid sample and sealed,
withdrawing the filled bag from said one section of said container after said other section thereof has been disconnected from said one section, and
thereafter reconnecting said sections of said container for use in a subsequent sample collecting operation with a new plastic bag.

7. A sample collector comprising in combination
a rigid, two-piece hollow container including an upper section having an annular neck portion defining and surrounding an inlet opening for said container, and a lower section releasably engaged with said upper section,
a flexible, plastic bag removably mounted in said container and having adjacent an upper end thereof an annular neck portion defining and surrounding an inlet/outlet opening in said bag,
bag supporting means releasably securing said neck portion of said bag coaxially in an open position over said neck portion of said upper section of said container, whereby said bag at its lower end extends downwardly into said lower section of said container and is removably supported upright in said container to permit a liquid sample to be fed through said neck portion thereof into said bag, and whereby said liquid sample is prevented by said bag from coming into contact with the interior of said container,
said upper section of said container having therein a small vent opening communicating at one end with a space between said upper section of said container and said bag, and at its opposite end with the exterior of said container, thereby to vent said space when a liquid sample is fed into the bag, and
said upper section of said container being selectively disengageable from said lower section to form in said container a second opening larger than said inlet opening for said container, whereby when said bag has been filled and released by said bag supporting means, the filled bag may be withdrawn from said container through said second opening.

8. A sample collector as defined in claim 7, wherein adjacent one edge thereof said lower section of said container is hingedly connected to an adjacent edge of said upper section thereof.

* * * * *